United States Patent
Martin et al.

(10) Patent No.: US 6,867,281 B2
(45) Date of Patent: Mar. 15, 2005

(54) HIGHLY CONDUCTING AND TRANSPARENT THIN FILMS FORMED FROM NEW FLUORINATED DERIVATIVES OF 3,4-ETHYLENEDIOXYTHIOPHENE

(75) Inventors: Brett D. Martin, Washington, DC (US); Ranganathan Shashidhar, Woodbridge, VA (US); Nikolay Nikolov, Woodbridge, VA (US); John C. Mastrangelo, Alexandria, VA (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 10/396,443

(22) Filed: Mar. 26, 2003

(65) Prior Publication Data
US 2004/0214985 A1 Oct. 28, 2004

(51) Int. Cl.$^7$ .............................................. C08G 75/00
(52) U.S. Cl. ...................... 528/373; 528/377; 528/401; 528/271; 528/364
(58) Field of Search ................................ 528/373, 377, 528/401, 271, 364

(56) References Cited

U.S. PATENT DOCUMENTS

| | | |
|---|---|---|
| 5,035,926 A | 7/1991 | Jonas et al. |
| 5,111,327 A | 5/1992 | Blohm et al. |
| 5,571,454 A | 11/1996 | Chen et al. |
| 5,766,515 A | 6/1998 | Jonas et al. |
| 5,929,182 A | 7/1999 | Zajaczkowski |
| 6,327,070 B1 | 12/2001 | Heuer et al. |

OTHER PUBLICATIONS

Skotheim et al, "Handbook of Conducting Polymers", Marcel Dekker Inc, 1998, pp. 323–326.

*Primary Examiner*—Duc Truong
(74) *Attorney, Agent, or Firm*—John J. Karasek; Joseph T. Grunkemeyer

(57) ABSTRACT

A compound comprising the formula:

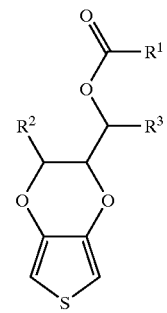

wherein $R^1$ is a fluorinated organic group and $R^2$ and $R^3$ are independently selected organic groups. A compound comprising the formula:

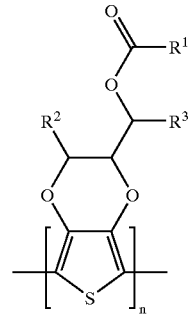

wherein $R^1$ is a fluorinated organic group and $R^2$ and $R^3$ are independently selected organic groups.

20 Claims, 7 Drawing Sheets

HIGHLY CONDUCTING AND TRANSPARENT THIN FILMS FORMED FROM NEW FLUORINATED DERIVATIVES OF 3,4-ETHYLENEDIOXYTHIOPHENE

BACKGROUND OF THE INVENTION

1. Field of the Invention

The invention relates generally to fluorinated derivatives of 3,4-ethylenedioxythiophene and polymers derived therefrom.

2. Description of the Prior Art

Conducting polymers can be used in organic light-emitting diodes (OLED's). OLED's are an attractive alternative to liquid crystal display technology because they can yield displays that are brighter, lower cost, consume less power, and are lightweight.

Extended π-conjugated conducting oligomers and polymers have unique properties that have impacted diverse technologies, and have resulted in the appearance of new ones. A partial list of current and developing applications includes micro- and nanoscale circuitry, throwaway electronic devices such as plastic electrochromic displays, lightweight storage batteries, corrosion protection coatings, antistatic coatings, bio- and chemical sensors, and military applications such as microwave-absorbing materials. In all of these applications a high degree of polymer transparency in visible wavelengths is either necessary or could represent an additional advantageous trait.

Key properties of π-conjugated conducting oligomers and polymers such as bandgap, dielectric constant, and oxidation potential can be varied over much wider ranges than those of other transparent inorganic conductors such as indium tin oxide (ITO) ceramic. This is because of the vast diversity inherent to the organic chemistry of π-conjugated monomers. Other advantages over metals and inorganics include greater plasticity and elasticity, lower mass density, lower coefficient of thermal expansion, greater resistance to chemicals and corrosion, electrochromism, and enhanced power storage capabilities.

As an example of a specific application wherein a highly transparent conducting polymer could have a large impact, one can consider the liquid crystal display devices (LCD's) that are extremely important in current information technology and OLED's under development for next generation displays. In these devices, or in any display device, transparent electrodes are a prime requirement and ITO coated on glass or clear plastic surfaces has generally been used up to now because of its high transparency (~90%), low surface resistance (~70 ohms/sq), and high conductivity (~1000 S/cm). However, the technology is quite expensive and requires high temperature and vacuum treatment. Moreover, the brittleness of the ITO, the non-stoichiometric nature of ITO surfaces, and poor adhesion at the inorganic-organic interface causes serious problems. The deposition of transparent, conductive polymer film on plastic substrates is a highly promising alternative that allows circumvention of these problems. FIGS. 1 and 2 schematically illustrate embodiments of a LCD (FIG. 1) and an OLED (FIG. 2).

Because conducting oligomers/polymers are highly conjugated, they may be colored both in the neutral undoped (non-conducting) state as well as in the cationic, doped (conducting) state. The development of highly transparent conducting polymer thin films has therefore been challenging. Prior art has centered on three families of conducting polymers, polyaniline (PANI), polypyrrole (PPY), and poly (3,4 alkylenethiophene) (PATP).

Jonas et al., U.S. Pat. No. 5,035,926 discloses single layer coatings of poly(3,4-dioxythiophene) made by surface polymerization.

U.S. Pat. No. 6,327,070 to Heuer et al. discloses PATP's with alkylidene groups such as ethylene, propylene, and butylene as well as those containing phenyl and tetradecyl moieties yielding films with modest properties when formed via electropolymerization. For example, poly(3,4 ethylenedioxythiophene) films had a conductivity of 8 S/cm with a transparency of 52%.

An attractive attribute of the monomeric alkylidenethiophenes is their low oxidation potential (~0.4 V relative to Ag/AgCl) that allows use of mild oxidation agents and results in polymer with high chemical stability. The polymers also have a low band gap (1.5–1.6 eV), causing their absorption $\lambda_{max}$ values to appear at relatively long wavelengths (590 nm for the undoped form and 775 nm for the doped form). The corresponding colors are dark violet and sky blue. The absorption in the doped conducting form is shifted into the infrared region and therefore the polymers become less heavily colored and are more transparent to the human eye. Within this class of conducting polymers, by far the most extensively investigated has been poly(3,4 ethylenedioxythiophene), or PEDOT, the simplest one from the standpoint of chemical structure. FIG. 3 illustrates the reaction scheme for the polymerization of PEDOT into both doped and undoped forms.

A polymerization method that is well suited for monomers with low oxidation potential such as PEDOT utilizes an oxidant, a base, and an alcohol solvent oxidant. At moderately high temperatures (~100° C.) the polymerization occurs very rapidly. De Leeuw et al., "Electroplating of Conductive Polymers for the Metallization of Insulators," *Synth. Metals*, 66(3), 263 discloses that if the reactant-containing solution is spin-coated onto a suitable substrate such as plastic or glass and then heated, highly conducting insoluble sky-blue films are formed. FIG. 4 illustrates the reaction scheme for the polymerization of PEDOT by surface polymerization. See also Kumar et al., "Conducting Poly(3,4-alkylenedioxythiophene) Derivatives as Fast Electrochromics with High-Contrast Ratios," *Chem. Mater.*, 10(3), 896 and Pei et al., "Electrochromic and Highly Stable Poly(3,4-ethylenedioxythiophene) Switches Between Opaque Blue-black and Transparent Sky Blue", *Polymer*, 35(7), 1347–1351.

U.S. Pat. No. 6,327,070 discloses 3,4-ethylenedioxythiophene (EDOT) derivatized with alkyl and aryl groups. Cycloalkyl, alkoxy, etheric, urea, sulfonate, and perfluoralkoxy derivatized 3,4-ethylenedioxythiophenes are disclosed in *Handbook of Conducting Polymers*, Skotheim et al., Marcell Dekker, New York 1998.

SUMMARY OF THE INVENTION

The invention comprises a compound comprising Formula (1):

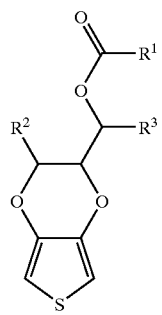

(1)

wherein $R^1$ is a fluorinated organic group and $R^2$ and $R^3$ are independently selected organic groups.

The invention also comprises a compound comprising Formula (2):

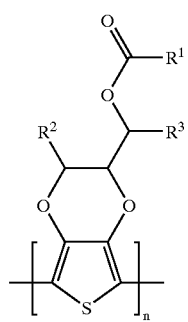

(2)

wherein $R^1$ is a fluorinated organic group and $R^2$ and $R^3$ are independently selected organic groups.

DETAILED DESCRIPTION OF THE PREFERRED EMBODIMENTS

Figure 1:
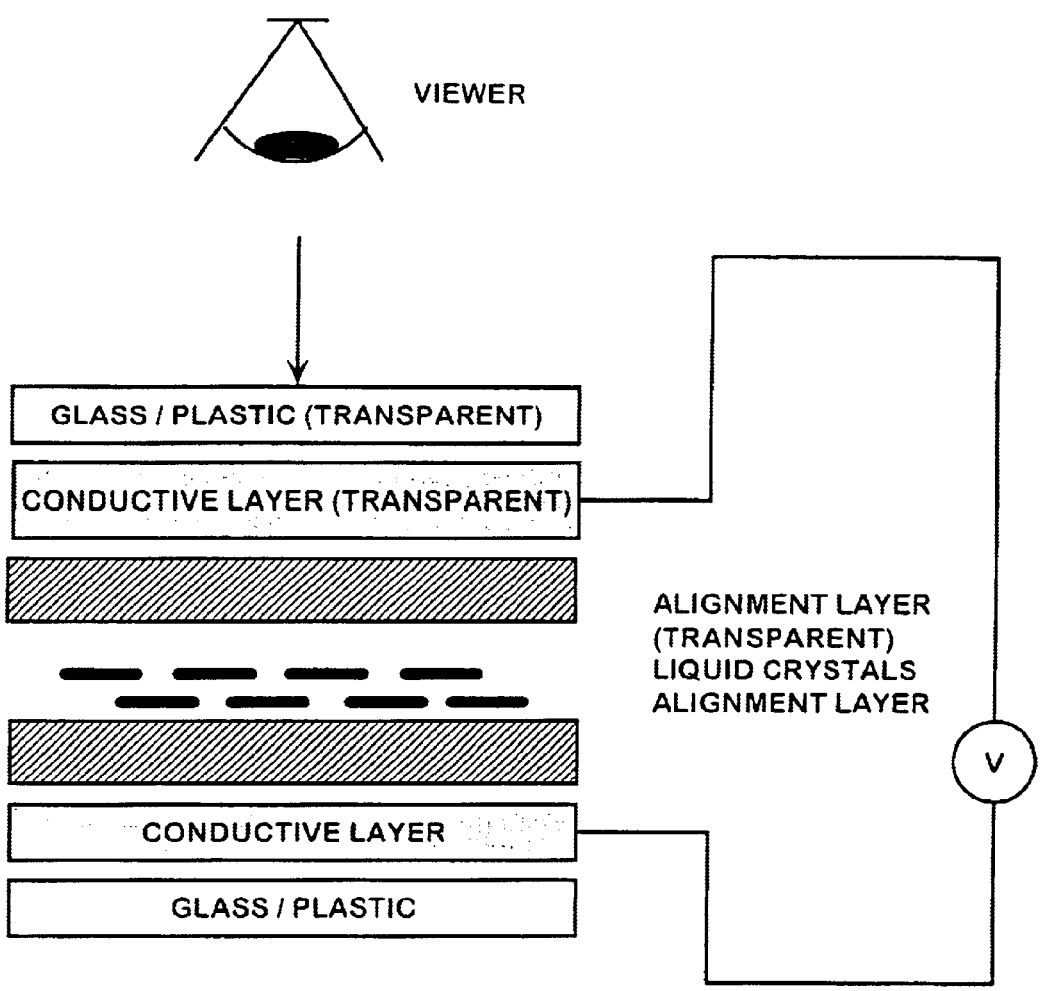
FIG. 1 is schematic illustration of the construction of an embodiment of a LCD device.
Figure 2:
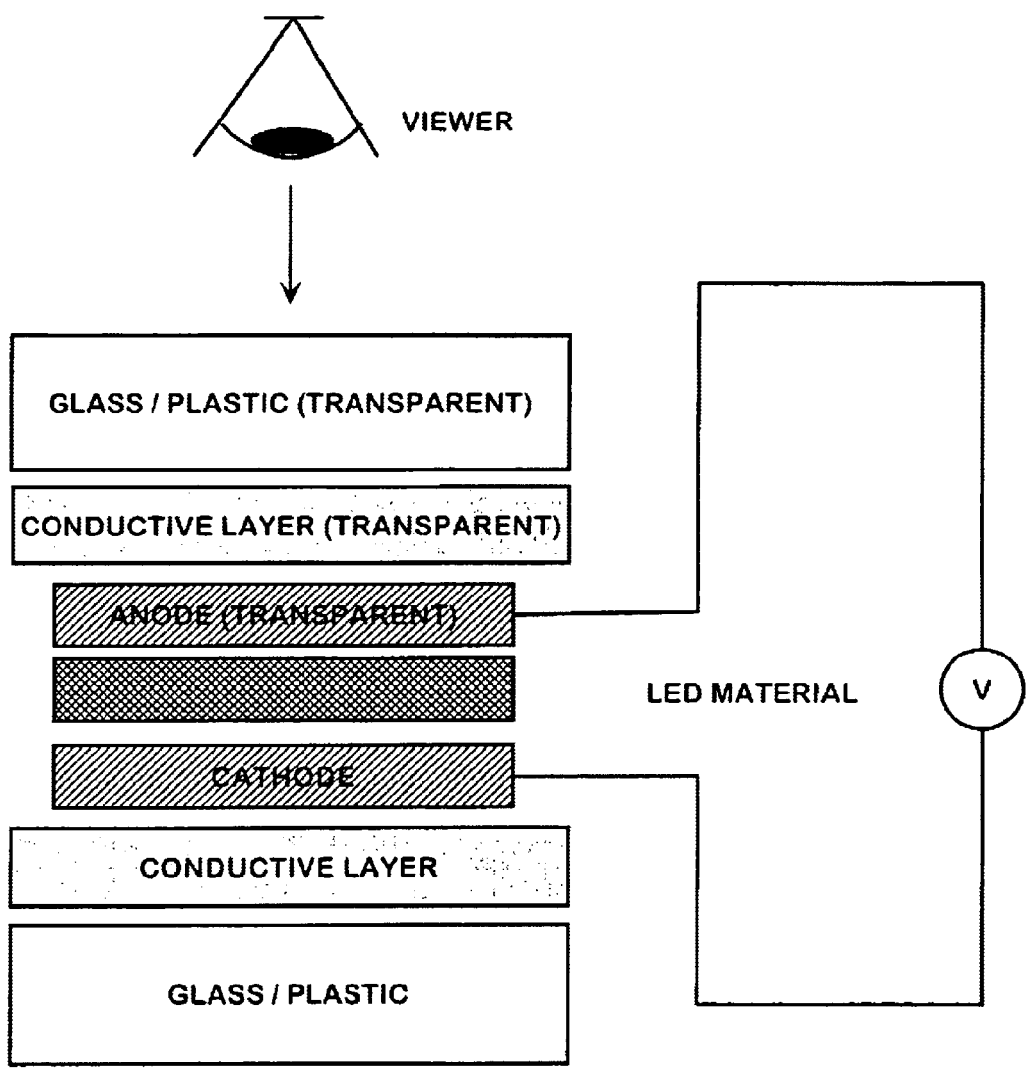
FIG. 2 is schematic illustration of the construction of an embodiment of an OLED device.
Figure 3:
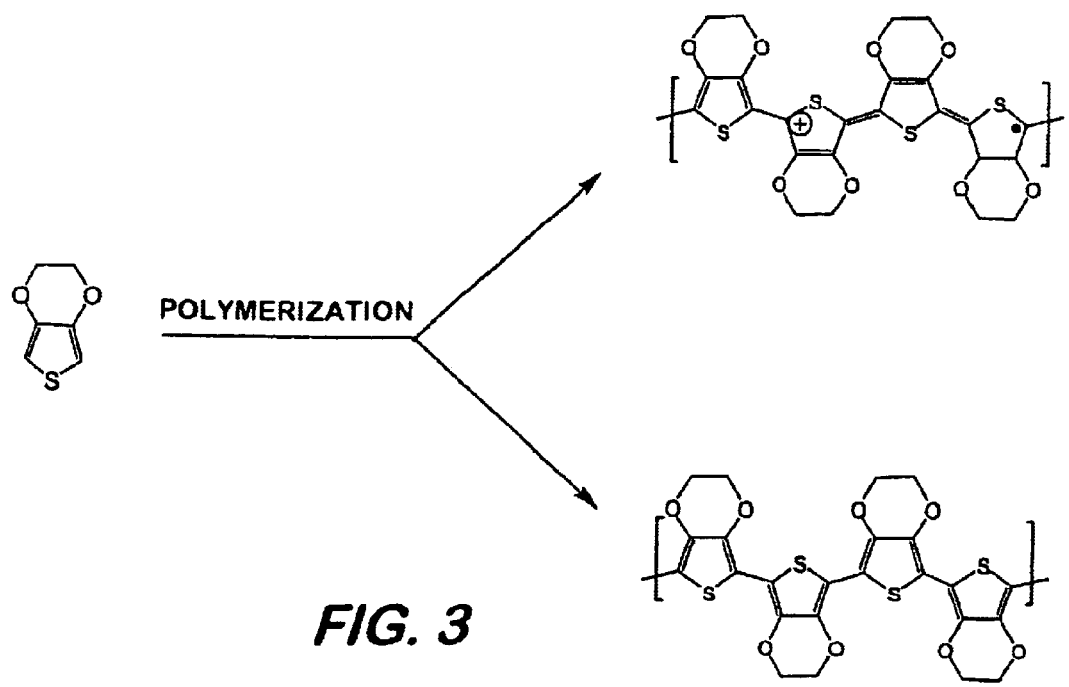
FIG. 3 illustrates the reaction scheme for the polymerization of PEDOT into both doped and undoped forms.
Figure 4:
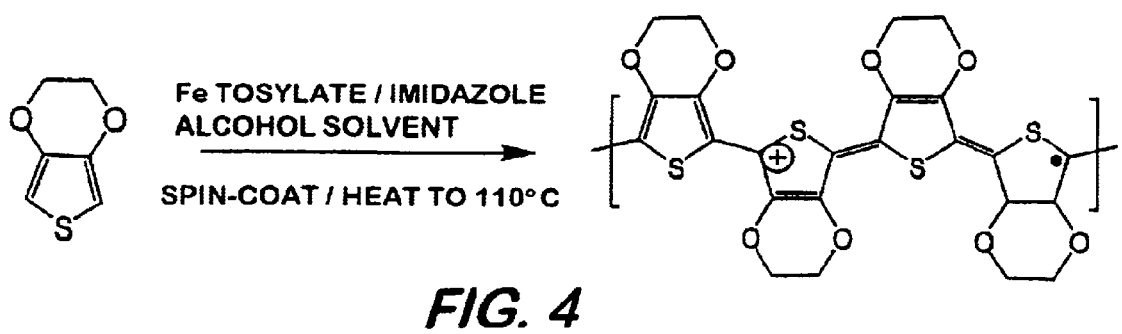
FIG. 4 illustrates the reaction scheme for the polymerization of PEDOT by surface polymerization.

The invention comprises new fluoromonomers based on 3,4-ethylenedioxythiophene (EDOT), and polymers derived therefrom. In particular, perfluoroalkylated poly(3,4 ethylenedioxythiophene) can have film conductivities as high as 600 S/cm with transparencies as great as 88% in the visible region of the spectrum. Underivatized poly(3,4 ethylenedioxythiophene) exhibits conductivities of only ~250 S/cm with similar transparencies.

The monomers may be synthesized by methods known in the art. Such methods include, but are not limited to, esterification of a hydroxymethylated form of EDOT, (2,3-dihydro-thieno[3,4-b][1,4]dioxin-2-yl)-methanol, and its derivatives. This precursor may be synthesized according to the procedure disclosed in Stephan et al., "Electrochemical behaviour of 3,4-ethylenedioxythiophene functionalized by a sulphonate group. Application to the preparation of poly (3,4-ethylenedioxythiophene) having permanent cation-exchange properties," J. Electroanal. Chem. 443, 217, incorporated herein by reference. The reaction scheme for the monomer is shown in Formula (3).

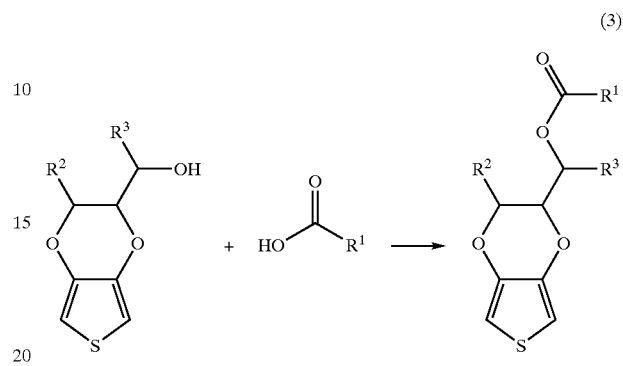

(3)

$R^1$ is a fluorinated organic group, and $R^2$ and $R^3$ are independently selected organic groups. As used herein, the term "organic groups" includes hydrogen and hydroxyl. $R^2$ and $R^3$ may both be H. $R^1$ may be a fluorinated organic group selected from the group consisting of alkyl, linear alkyl having from 1 to 14 carbon atoms, aromatic, cycloaliphatic, carbohydrate, amine, ketone, ether, alkenyl, alkynyl, secondary amine, tertiary amine, thione, sulfide, sulfonate, sulfate, phosphine, phosphate, and phosphonate. Suitable fluorinated groups include, but are not limited to peffluoroalkyl, 1,1,2,2,3,3,4,4,4-nonafluorobutyl, and 1,1,2,2,3,3,4,4,5,5,6,6,7,7,8,8,8-heptadecylfluorooctyl. The latter two monomers are shown in Formula (4).

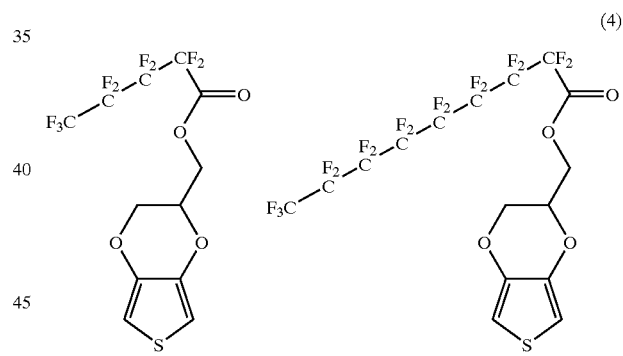

(4)

The monomers may be polymerized by any method according to the scheme shown in Formula (5). Such methods are known in the art. The polymer in Formula (5) may be a homopolymer when a single monomer is used or may have more than one monomer.

(5)

The polymerization can be done by surface polymerization. This may be done by spin-coating a solution comprising the monomer, an oxidant, a base, and an alcohol solvent onto a substrate. This mixture may catalyze the polymerization of the monomer. Iron (III) p-toluenesulfonate is a suitable oxidant and imidazole is a suitable base. 1-Butanol and 2-methoxyethanol are suitable solvents. The substrate is then heated to produce the polymer.

The polymer may have a conductivity of at least about 100 S/cm and a transparency of at least about 80%. Surface polymerization can produce a thin film of the polymer. Such films may be useful in display devices. A combination of 100 ohms (500 S/cm) and 85% T is desirable for display devices.

The fluorinated groups may be capable of self-assembly, which may improve the conductivity of the polymer. The self-assembling moieties may drive the EDOT moieties into an ordered arrangement that may allow greater charge mobility (cation or "hole" transport), and thus the film may experience lowered surface resistance and a higher conductivity. The perfluoroalkyl-derivatized polymer films may have conductivities approximately twice as high as those formed from underivatized EDOT, with comparable or slightly higher film transparencies in the visible wavelengths (see Examples below). These desirable properties may arise from fluorophilic attractive forces that lead to productive monomer or polymer self-assembly.

The advantages of the monomers, including 2,2,3,3,4,4, 5,5,5-nonafluoro-pentanoic acid 2,3dihydro-thieno[-3,4b][1, 4]dioxin-2-yl methyl ester ("$C_4F_9$-EDOT") and 2,2,3,3,4,4, 5,5,6,6,7,7,8,8,9,9,9-heptadecylfluoro-nonanoic acid 2,3-dihydro-thieno[3,4-b][1,4]dioxin-2-ylmethyl ester ("$C_8F_{17}$-EDOT"), are the superior values of low electrical surface resistance, high conductivity, and high transparency when cast into thin films and polymerized. Other conducting polymers such as the closely related underivatized PEDOT, alkyl-derivatized PEDOT, polythiophene, alkyl-derivatized polythiophene, polypyrrole, and polyaniline may have higher surface resistances, lower conductivities, and/or lower transparencies when spin-cast into films.

Having described the invention, the following examples are given to illustrate specific applications of the invention. These specific examples are not intended to limit the scope of the invention described in this application.
Synthesis and Characterization of EDOT Derivatives The EDOT derivatives were synthesized by esterification of a hydroxymethylated form of EDOT, (2,3-Dihydro-thieno[3,4-b][1,4]dioxin-2-yl)-methanol. This precursor was synthesized according to the procedure given in Stephan et al., *J. Electroanal. Chem.*, 443, 217.

EXAMPLE 1

Synthesis and Characterization of Synthesis of 2,2, 3,3,4,4,5,5,5-nonafluoro-pentanoic acid 2,3-dihydro-thieno[3,4-b][1,4]dioxin-2-ylmethyl ester ("$C_4F_9$-EDOT")

A solution of (2,3-Dihydro-thieno[3,4-b][1,4]dioxin-2-yl)-methanol ("hydroxymethyl EDOT", 1.20 g, 6.97 mmol) in dichloromethane (30 mL) was chilled to 0° C. under argon. Neat 2,2,3,3,4,4,5,5,5-nonafluoropentanoic acid (1.93 g, 7.35 mmol) was added by pipette. Quickly 1-[3-(dimethylamino)propyl]-3-ethylcarbodiimide methiodide (2.30 g, 7.80 mmol) and 3,4-dimethylaminopyridine (0.1 g, 0.82 mmol) were added and the solution was allowed to come to room temperature overnight. The solvent was evaporated at <30° C. and the residue purified by repeated column chromatography on silica gel using a gradient elution starting with 3:1 hexane/dichloromethane and ending with 1:1 hexane/dichloromethane. The product (2.10 g, 5.02 mmol) was a colorless oil that solidifies at −20° C. (Formula (4), left-hand side). Overall product yield was 53%.

Figure 5:
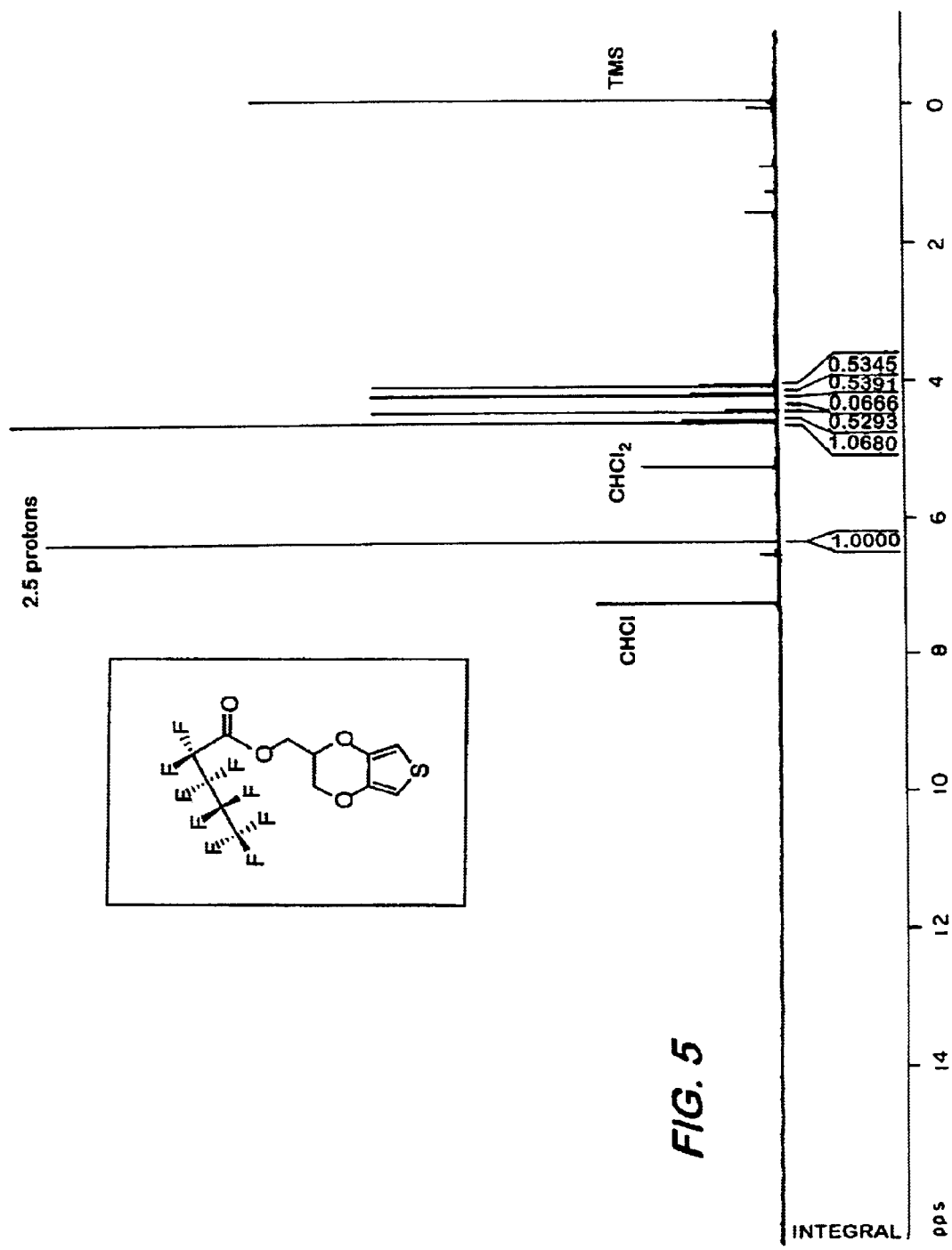
FIG. 5 is a $^1$H NMR spectrum of $C_4F_9$-EDOT.
Figure 6:
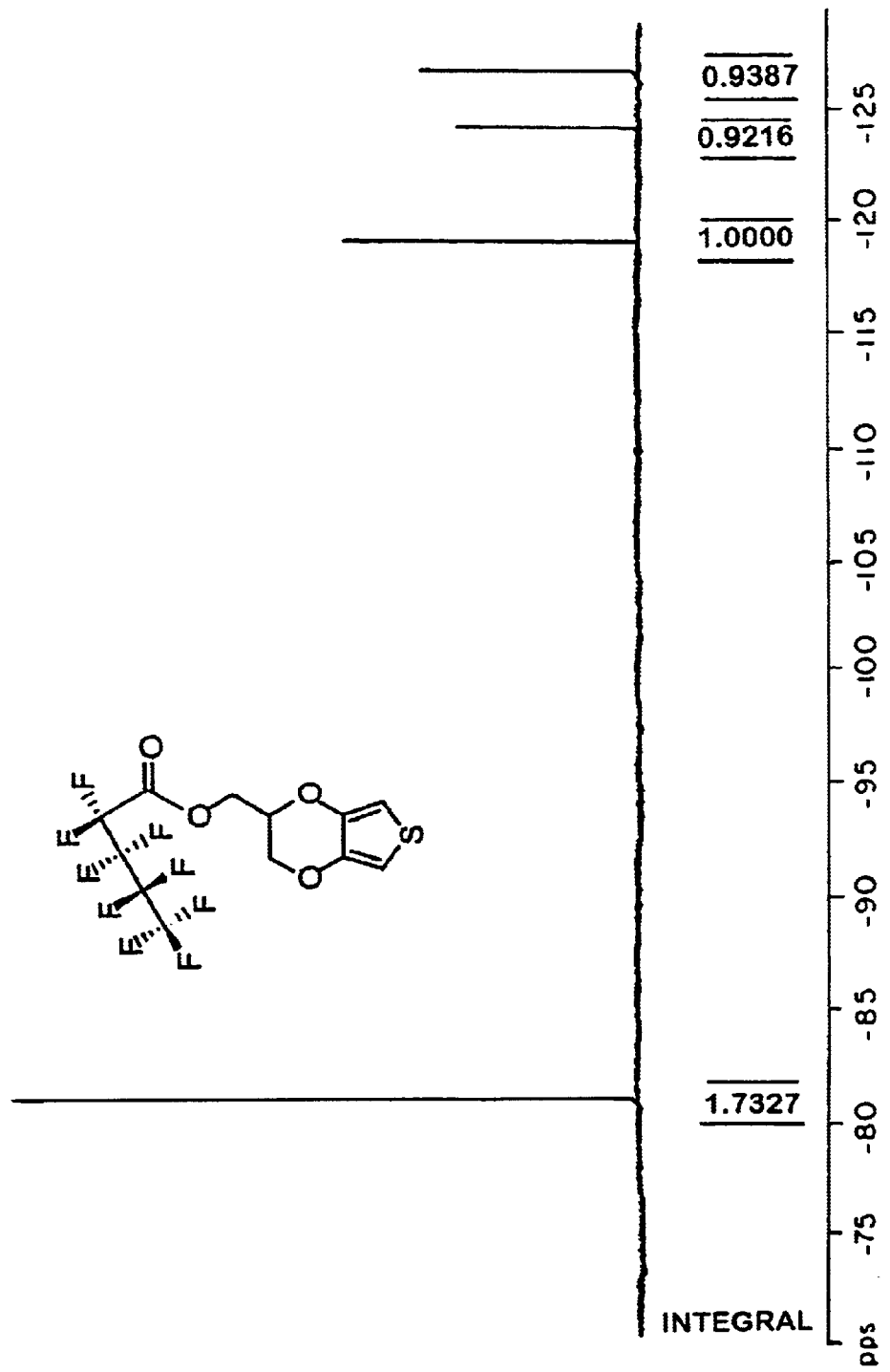
FIG. 6 is a $^{19}$F NMR of $C_4F_9$-EDOT.

The $C_4F_9$-EDOT was characterized using GC-MS, which yielded the expected m/z ratio of 418, the monomer MW. It was further characterized using $^1$H NMR (FIG. 5) and $^{19}$F NMR (FIG. 6). In FIG. 5, the protons at the 2- and 5-positions of the heterocycle are seen at 6.4 ppm, as expected, and the methylene protons α- to the ester oxygen appear at 4.6 ppm. The synthesis yields four isomers of $C_4F_9$-EDOT. This occurs because four isomers of the hydroxymethyl EDOT precursor are present. The strain-reducing twist of the ethylene moiety causes each of its carbons to become a chiral center. The proton(s) associated with each chiral center appear in the range 4.0 to 4.5 ppm. The $^{19}$F NMR verifies the presence of the perfluoroalkyl group, with the four different environments experienced by the F atoms represented by signals at −81 ppm, −119 ppm, −123.5 ppm, and −126.5 ppm. The relative peak intensities are 1.73, 1.00, 0.922, and 0.939, respectively.

EXAMPLE 2

Synthesis and Characterization of Synthesis of 2,2, 3,3,4,4,5,5,6,6,7,7,8,8,9,9,9-heptadecylfluoro-nonanoic Acid 2,3-dihydro-thieno[3,4-b][1,4]dioxin-2-ylmethyl Ester ("$C_8F_{17}$-EDOT")

A solution of (2,3-Dihydro-thieno[3,4-b][1,4]dioxin-2-yl)-methanol (0.71 g 4.12 mmol) in THF (15 mL) was chilled to 0° C. under argon. Neat 2,2,3,3,4,4,5,5,6,6,7,7,8, 8,9,9,9-heptadecylfluoro-nonanoic acid (2.11 g, 4.54 mmol) was added by pipette. Quickly 1-[3-(dimethylamino)propyl]-3-ethylcarbodiimide methiodide (1.46 g, 4.91 mmol) and 3,4-dimethylaminopyridine (0.14 g, 1.15 mmol) were added and the solution was allowed to come to room temperature overnight. The solvent was evaporated at <30° C. and the residue purified by repeated column chromatography on silica gel using a gradient elution starting with 3:1 hexane/dichloromethane and ending with 1:1 hexane/dichloromethane. The product (1.16 g, 1.19 mmol) was light yellow waxy solid (Formula (4), right-hand side). Overall product yield was 45%.

Figure 7:
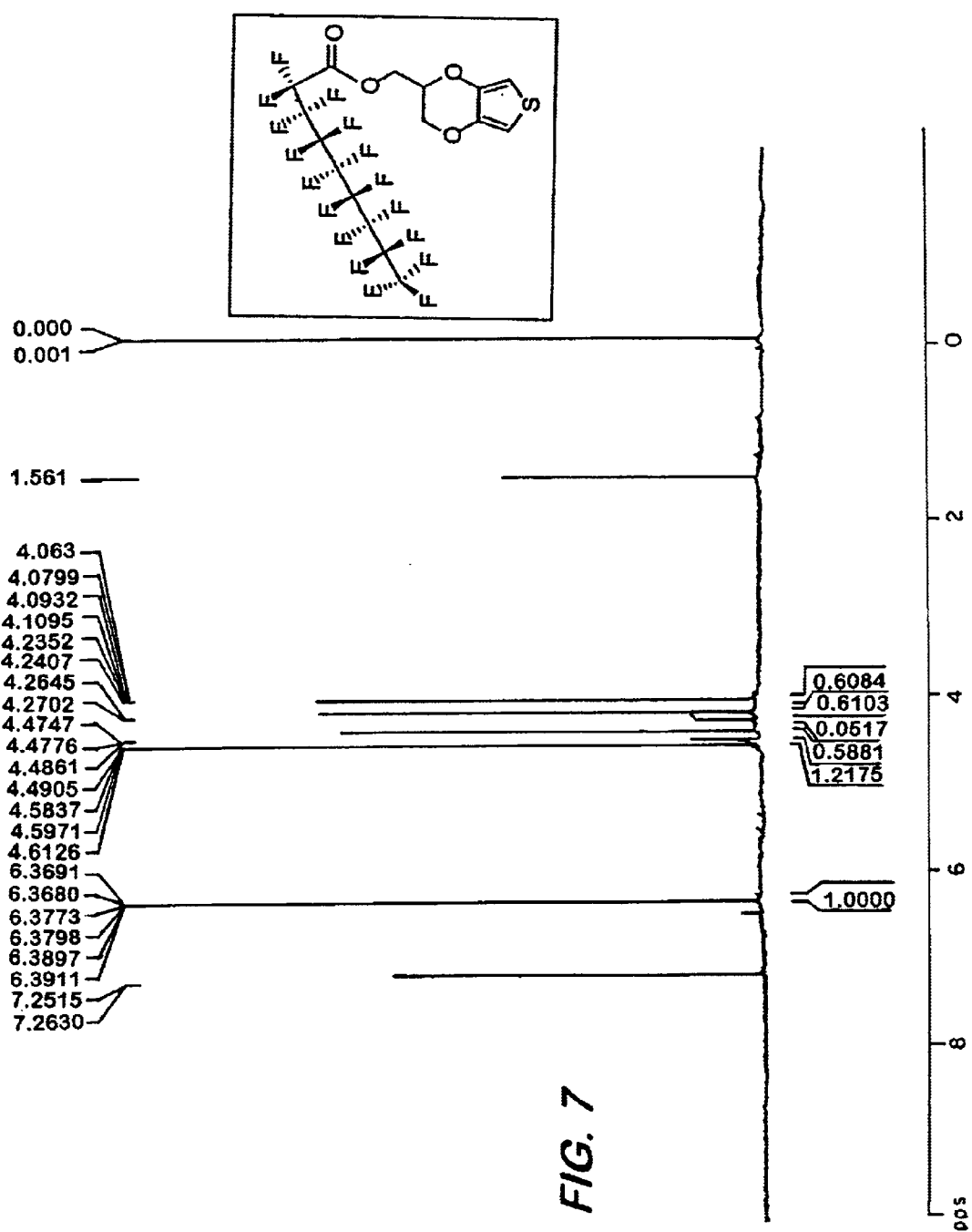
FIG. 7 is a $^1$H NMR spectrum of $C_8F_{17}$-EDOT.

The $C_8F_{17}$-EDOT was characterized using GC-MS, which yielded the expected m/z ratio of 618, the monomer MW. It was further characterized using $^1$H NMR (FIG. 7). In FIG. 7, the protons at the 2- and 5-positions of the heterocycle are seen at 6.4 ppm, as expected, and the methylene protons α- to the ester oxygen appear at 4.6 ppm. As in the synthesis of $C_4F_9$-EDOT, the synthesis of $C_8F_{17}$-EDOT yields four isomers. The proton(s) associated with each chiral center appear in the range 4.0 to 4.5 ppm.
Surface Polymerization of Monomers There are six fundamental process variables for the surface polymerization process: monomer concentration, molar ratio between solutes, choice of alcohol solvent, spin-coating speed in RPM, polymerization temperature, and polymerization time. It was determined that the polymer films could be formed using various ranges of three process variables and fixed values or types of the other three (Table 1).

TABLE 1

Process variables for spin coating polymerization of $C_4F_9$-EDOT and $C_8F_{17}$-EDOT

| Variable | Range or type |
| --- | --- |
| Total solute concentration | 30–50 wt % |
| Molar ratio - monomer:oxidant:base | 1:2.6:2, 1:2:2, 1:1.75:2, 1:1.5:2 |
| Solvent | butanol |
| Spin speed | 100–8000 RPM |
| Polymerization time | 2 minutes |
| Polymerization temperature | 110° C. |

EXAMPLE 3

Surface Polymerization of $C_4F_9$-EDOT

Thin polymer films were formed from the monomer in a spin-coating process. In a typical polymerization, the $C_4F_9$-EDOT was dissolved in an alcohol solvent, i.e. 1-butanol, in a concentration of 0.33 M, e.g. 418 mg monomer in 3 mL solvent. 136 mg imidazole was then added, giving a concentration of 0.66 M. 1.35 g of the oxidant, iron (III) toluene sulfonate hexahydrate, was then added, giving a concentration of 0.66 M. The total concentration of solute was 39 wt %. The solution was immediately spin-coated at 3000, 4000, or 5000 RPM onto 2.5 cm×2.5 cm square PET plastic films of nominal thickness 0.1 mm. Each spin speed yielded a film of different thickness with higher speeds giving thinner films. To form the polymer film, the films were immediately heated at atmospheric pressure to 110° C. for 3 min. They were then rinsed with methanol and surface resistance and transparency measurements were taken.

For the $C_4F_9$-EDOT polymerization, butanol is a suitable solvent. The reactant molar ratio given above resulted in films with the most optimal properties achieved with this monomer, i.e. lowest surface resistance, highest conductivity, and highest transparency. The chemical structure of the polymer film is shown in Formula (6).

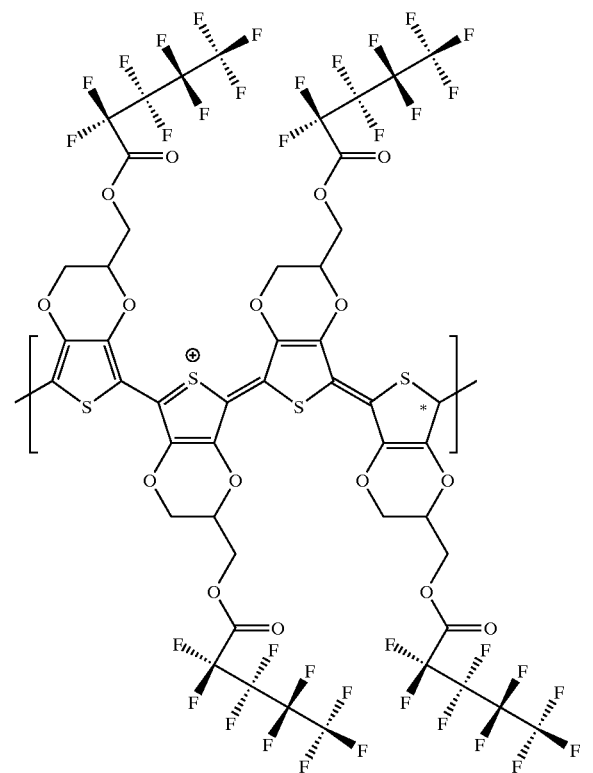

(6)

Figure 8:
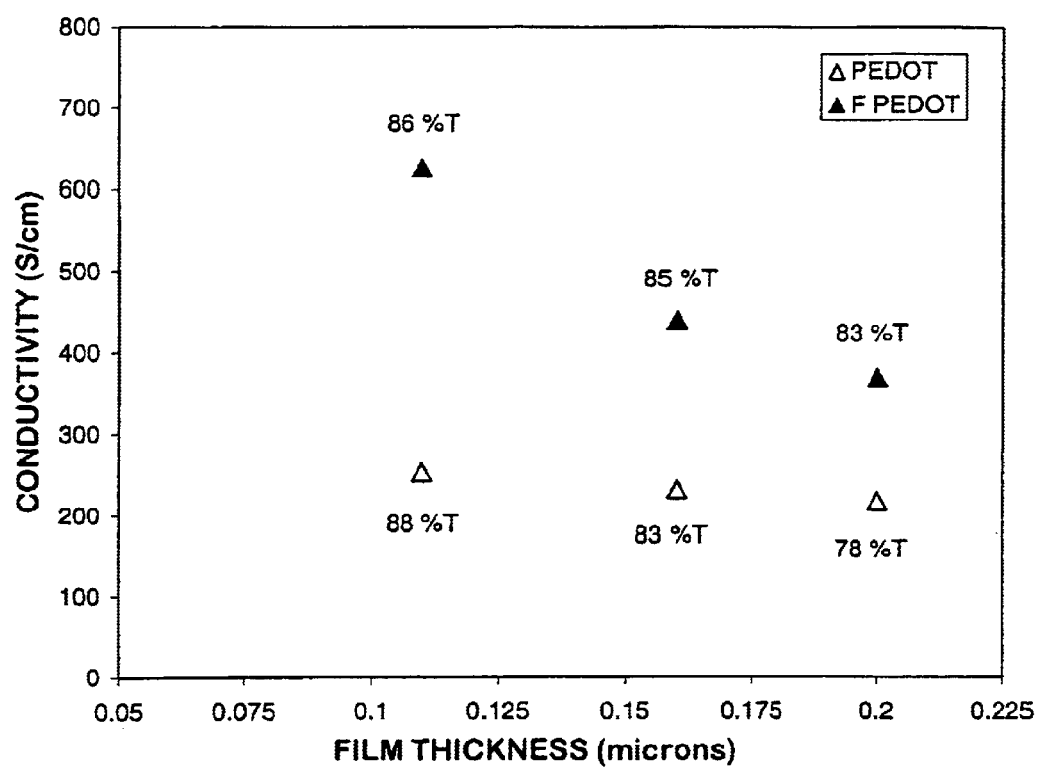
FIG. 8 is a comparison of poly(EDOT) films (open triangles) and poly($C_4F_9$ EDOT) films (filled triangles).

The polymer has conductivities and transparencies properties superior to poly(EDOT) formed from underivatized EDOT, as shown in FIG. 8. For this comparison, EDOT was polymerized in a manner highly similar to that described in Example 3. EDOT was dissolved in an alcohol solvent, i.e. 2-methoxyethanol, in a concentration of 0.33 M. Imidazole was then added, giving a concentration of 0.66 M. The oxidant, iron (III) toluene sulfonate hexahydrate, was then added, giving a concentration of 0.66 M. The total concentration of solute was 36 wt %. The solution was immediately spin-coated at 3000, 4000, or 5000 RPM onto 2.5 cm×2.5 cm square PET plastic films of nominal thickness 0.1 mm. To form the polymer film, the films were immediately heated at atmospheric pressure to 110° C. for 3 min. They were then rinsed with methanol and surface resistance and transparency measurements were taken.

For the EDOT polymerization, 2-methoxyethanol was used as the solvent. The reactant molar ratio given above resulted in films with the most optimal properties achieved with this monomer, i.e. lowest surface resistance, highest conductivity, and highest transparency.

EXAMPLE 4

Surface Polymerization of $C_8F_{17}$-EDOT

The $C_8F_{17}$-EDOT was polymerized in a similar manner. In a typical polymerization, the monomer was dissolved in an alcohol solvent, i.e. n-butanol, in a concentration of 0.33 M. As in Example 3, imidazole was then added, giving a concentration of 0.66 M, and the oxidant iron (III) toluene sulfonate hexahydrate was then added, giving a concentration of 0.58 M. The total concentration of solute was 42 wt %. The solution was immediately spin-coated at 3000 RPM onto 2.5 cm×2.5 cm square PET plastic films of nominal thickness 0.1 mm. To form the polymer film, the films were immediately heated at atmospheric pressure to 110° C. for 3 min. They were then rinsed with methanol and surface resistance and transparency measurements were taken. The chemical structure of the polymer is shown in Formula (7). The film surface resistances and transparencies are given in Table 2.

For the $C_8F_{17}$-EDOT polymerization, butanol is a suitable solvent. The reactant molar ratio given above resulted in films with the optimal properties achieved with this monomer, i.e. lowest surface resistance, highest conductivity, and highest transparency.

TABLE 2

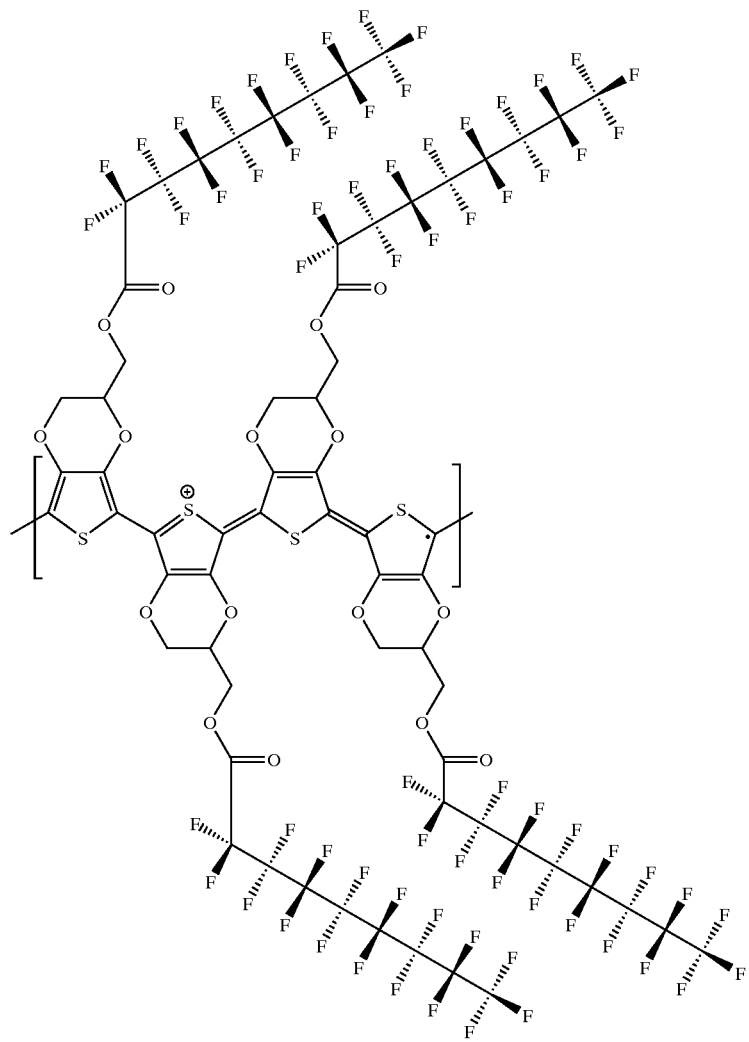

(7)

Summary of Film Properties at 3000 RPM

| property | $C_8F_{17}$-PEDOT | $C_4F_9$-PEDOT | PEDOT |
|---|---|---|---|
| resistance (Ω) | 210 | 190 | 270 |
| % T | 87 | 85 | 83 |

As is clearly seen in Table 2, the polymer films formed from the perfluoroalkyl-containing monomers have properties superior to underivatized PEDOT.

The co-filed U.S. Patent Application to Martin et al., "Highly Conducting and Transparent Thin Films Formed from Double and Multiple Layers of Poly(3,4-ethylenedioxythiophene) and its Derivatives," designated as Navy Case 84,102 is incorporated herein by reference.

We claim:

1. A compound comprising the formula:

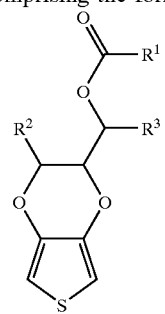

wherein $R^1$ is a fluorinated organic group and $R^2$ and $R^3$ are independently selected organic groups.

2. The compound of claim 1, wherein $R^2$ and $R^3$ are both H.

3. The compound of claim 2, wherein $R^1$ is a fluorinated organic group selected from the group consisting of alkyl, linear alkyl having from 1 to 14 carbon atoms, aromatic, cycloaliphatic, carbohydrate, amine, ketone, ether, alkenyl, alkynyl, secondary amine, tertiary amine, thione, sulfide, sulfonate, sulfate, phosphine, phosphate, and phosphonate.

4. The compound of claim 2, wherein $R^1$ is perfluoroalkyl.

5. The compound of claim 2, wherein $R^1$ is 1,1,2,2,3,3,4,4,4-nonafluorobutyl.

6. The compound of claim 2, wherein $R^1$ is 1,1,2,2,3,3,4,4,5,5,6,6,7,7,8,8,8-heptadecylfluorooctyl.

7. A compound comprising the formula:

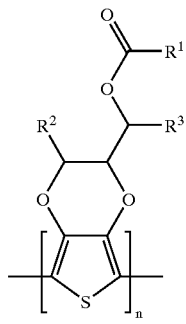

wherein $R^1$ is a fluorinated organic group and $R^2$ and $R^3$ are independently selected organic groups.

8. The compound of claim 7, wherein the compound is a homopolymer.

9. A film formed from the compound of claim 7.

10. The compound of claim 7, wherein $R^2$ and $R^3$ are both H.

11. The compound of claim 10, wherein $R^1$ is a the fluorinated group is selected from the group consisting of alkyl, linear alkyl having from 1 to 14 carbon atoms, aromatic, cycloaliphatic, carbohydrate, amine, ketone, ether, alkenyl, alkynyl, secondary amine, tertiary amine, thione, sulfide, sulfonate, sulfate, phosphine, phosphate, and phosphonate.

12. The compound of claim 10, wherein $R^1$ is perfluoroalkyl.

13. The compound of claim 10, wherein $R^1$ is 1,1,2,2,3,3,4,4,4-nonafluorobutyl.

14. A film formed from the compound of claim 13.

15. A film formed from the compound of claim 13, wherein the film is made by surface polymerization.

16. The compound of claim 10, wherein $R^1$ is 1,1,2,2,3,3,4,4,5,5,6,6,7,7,8,8,8-heptadecylfluorooctyl.

17. A film formed from the compound of claim 16.

18. A film formed from the compound of claim 16, wherein the film is made by surface polymerization.

19. The compound of claim 10, wherein the compound has a conductivity of at least about 100 S/cm and a transparency of at least about 80%.

20. A display device comprising the compound of claim 7.

* * * * *